(12) United States Patent
Zheng et al.

(10) Patent No.: US 9,895,083 B2
(45) Date of Patent: Feb. 20, 2018

(54) NON-INVASIVE VENTILATION MEASUREMENT

(75) Inventors: Han Zheng, Carlsbad, CA (US); Samir Ahmad, San Diego, CA (US); Masahiro Taniguchi, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 544 days.

(21) Appl. No.: 14/237,937

(22) PCT Filed: Jul. 25, 2012

(86) PCT No.: PCT/IB2012/053777
§ 371 (c)(1),
(2), (4) Date: Feb. 10, 2014

(87) PCT Pub. No.: WO2013/027137
PCT Pub. Date: Feb. 28, 2013

(65) Prior Publication Data
US 2014/0194767 A1    Jul. 10, 2014

Related U.S. Application Data

(60) Provisional application No. 61/527,186, filed on Aug. 25, 2011.

(51) Int. Cl.
A61B 5/08     (2006.01)
A61B 5/087    (2006.01)
(Continued)

(52) U.S. Cl.
CPC ........... *A61B 5/087* (2013.01); *A61B 5/03* (2013.01); *A61M 16/0051* (2013.01);
(Continued)

(58) Field of Classification Search
CPC ........ A61B 5/087; A61B 5/03; A61M 16/161; A61M 16/0051; A61M 2205/3365;
(Continued)

(56) References Cited

U.S. PATENT DOCUMENTS 6,257,234 B1 *  7/2001  Sun .................... A61M 16/0051
                                                      128/204.18
6,837,242 B2    1/2005  Younes
(Continued)

FOREIGN PATENT DOCUMENTS

CN    1191546 A     8/1998
CN    102056538 A   5/2011
(Continued)

OTHER PUBLICATIONS

"Compliance (physiology)." https://en.wikipedia.org/wiki/Compliance_(physiology).*
(Continued)

*Primary Examiner* — Tiffany Weston (57) ABSTRACT

Determining the lung compliance and lung resistance of a subject undergoing respiratory therapy using non-invasive ventilation requires taking the presence of leaks into account. In particular, variable and unintentional leaks at or near a subject interface appliance may be dynamically determined based on an average resistance of the leak orifice of the subject.

20 Claims, 3 Drawing Sheets

(51) Int. Cl.
*A61B 5/03* (2006.01)
*A61M 16/00* (2006.01)
*G09B 23/28* (2006.01)
*A61M 16/16* (2006.01)

(52) U.S. Cl.
CPC ......... *A61M 16/161* (2014.02); *G09B 23/288* (2013.01); *A61M 2016/0027* (2013.01); *A61M 2016/0033* (2013.01); *A61M 2205/15* (2013.01); *A61M 2205/3365* (2013.01); *A61M 2205/3368* (2013.01); *A61M 2205/502* (2013.01); *A61M 2205/52* (2013.01); *A61M 2230/46* (2013.01)

(58) Field of Classification Search
CPC .......... A61M 2205/15; A61M 2205/52; A61M 2205/3368; A61M 2230/46; A61M 2016/0027; A61M 2205/502; A61M 2016/0033; G09B 23/288
See application file for complete search history.

(56) References Cited

U.S. PATENT DOCUMENTS

| | | |
|---|---|---|
| 7,322,937 B2 | 1/2008 | Blomberg et al. |
| 7,425,201 B2 | 9/2008 | Euliano et al. |
| 2006/0249150 A1 | 11/2006 | Dietz et al. |
| 2010/0071696 A1* | 3/2010 | Jafari ..................... A61B 5/085 128/204.23 |
| 2010/0236553 A1* | 9/2010 | Jafari ................ A61M 16/0051 128/204.21 |
| 2010/0236555 A1 | 9/2010 | Jafari et al. |

FOREIGN PATENT DOCUMENTS

| | | |
|---|---|---|
| JP | H06343623 A | 12/1994 |
| JP | 2003531694 A | 10/2003 |
| JP | 2004167252 A | 6/2004 |
| JP | 2005537068 A | 12/2005 |
| JP | 2008000436 A | 1/2008 |
| JP | 2008178695 A | 8/2008 |
| WO | 9705171 A1 | 2/1997 |
| WO | 0010634 A1 | 3/2000 |
| WO | 2009123979 A1 | 10/2009 |
| WO | 2009149353 A1 | 12/2009 |
| WO | 2010036653 A1 | 4/2010 |
| WO | 2010070498 A1 | 6/2010 |
| WO | 2011027242 A1 | 3/2011 |
| WO | WO 2011/027242 * 3/2011 ............... A61B 5/08 |

OTHER PUBLICATIONS

Jonathon D. Truwit et al, "Evaluation of Thoracic Mechanics in the Ventilated Patient: Applied Mechanics", Journal of Critical Care, Grune and Stratton, Orlando, FL., U.S., vol. 3. No. 3, Sep. 1, 1988, pp. 199-213, XP023060153, ISSN: 0883-9441.

* cited by examiner

NON-INVASIVE VENTILATION MEASUREMENT

CROSS-REFERENCE TO PRIOR APPLICATIONS

This application is the U.S. National Phase application under 35 U.S.C. § 371 of International Application No. PCT/IB2012/053777, filed on Jul. 25, 2012, which claims the benefit of U.S. Provisional Patent Application No. 61/527,186, filed on Aug. 25, 2011. These applications are hereby incorporated by reference herein.

BACKGROUND

1. Field

The present disclosure pertains to systems and methods for measuring respiratory parameters of a subject during application of non-invasive respiratory therapy, and, in particular, to measuring lung compliance and lung resistance on a breath-by-breath basis during spontaneous breathing and/or non-spontaneous breathing of the subject undergoing respiratory therapy.

2. Description of the Related Art

It is well known that the proper administration of respiratory therapy hinges on having accurate and up-to-date information regarding the lung mechanics of a patient (a.k.a a subject). Lung mechanics may include lung compliance, lung resistance, and/or other parameters. Respiratory therapy involving invasive mechanical ventilation is well-known, and during application of such therapy a monitor device can measure, e.g., subject flow in order to determine, e.g., lung compliance and/or lung resistance. Respiratory therapy involving non-invasive mechanical ventilation is well-know. However, during application of this type of therapy accurate and up-to-date information regarding the lung mechanics of a subject cannot usually be determined due to leaks in the system. Leaks may be intentional or non-intentional, known or unknown, variable or non-variable. In particular, non-intentional, unknown, and/or variable leaks may preclude the determination of accurate and up-to-date information regarding the lung mechanics of a subject.

SUMMARY

Accordingly, it is an object of one or more embodiments of the present disclosure to provide a system configured to measure respiratory parameters during application of non-invasive respiratory therapy of a subject. The system includes a timing module, a passive compliance module, a passive resistance module, an active compliance module, and an active resistance module. The timing module is configured to determine transitions between inhalations and exhalations. The passive compliance module is configured to determine a passive exhalation lung compliance during an exhalation, wherein the determination by the passive compliance module is based on a passive lung model, and wherein the exhalation is demarcated based on the transitions. The passive resistance module is configured to determine a passive exhalation lung resistance during the exhalation, wherein the determination by the passive resistance module is based on a passive lung model. The active compliance module is configured to determine an active lung compliance that reflects an active lung model, wherein the active lung compliance is determined based on the passive exhalation lung compliance and a subject breathing mode. The active resistance module is configured to determine an active lung resistance that reflects an active lung model, wherein the active lung resistance is determined based on the passive exhalation lung resistance and the subject breathing mode.

It is yet another aspect of one or more embodiments of the present disclosure to provide a method for measuring respiratory parameters during non-invasive respiratory therapy of a subject. The method comprises determining transitions in breathing between inhalations and exhalations; determining a passive exhalation lung compliance, during an exhalation, based on a passive lung model, wherein the exhalation is demarcated based on the transitions; determining a passive exhalation lung resistance, during the exhalation, based on the passive lung model; obtaining a subject breathing mode; determining an active lung compliance that reflects an active lung model, wherein the determination is based on the passive exhalation lung compliance and the subject breathing mode; and determining an active lung resistance that reflects an active lung model, wherein the determination is based on the passive exhalation lung resistance and the subject breathing mode.

It is yet another aspect of one or more embodiments to provide a system configured for measuring respiratory parameters during application of non-invasive respiratory therapy of a subject. The system comprises means for determining transitions in breathing between inhalations and exhalations; means for determining a passive exhalation lung compliance, during an exhalation, based on a passive lung model, wherein the exhalation is demarcated based on the transitions; means for determining a passive exhalation lung resistance, during the exhalation, based on the passive lung model; means for obtaining a subject breathing mode; means for determining an active lung compliance, reflecting an active lung model, based on the passive exhalation lung compliance and the subject breathing mode; and means for determining an active lung resistance, reflecting an active lung model, based on the passive exhalation lung resistance and the subject breathing mode.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals may designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
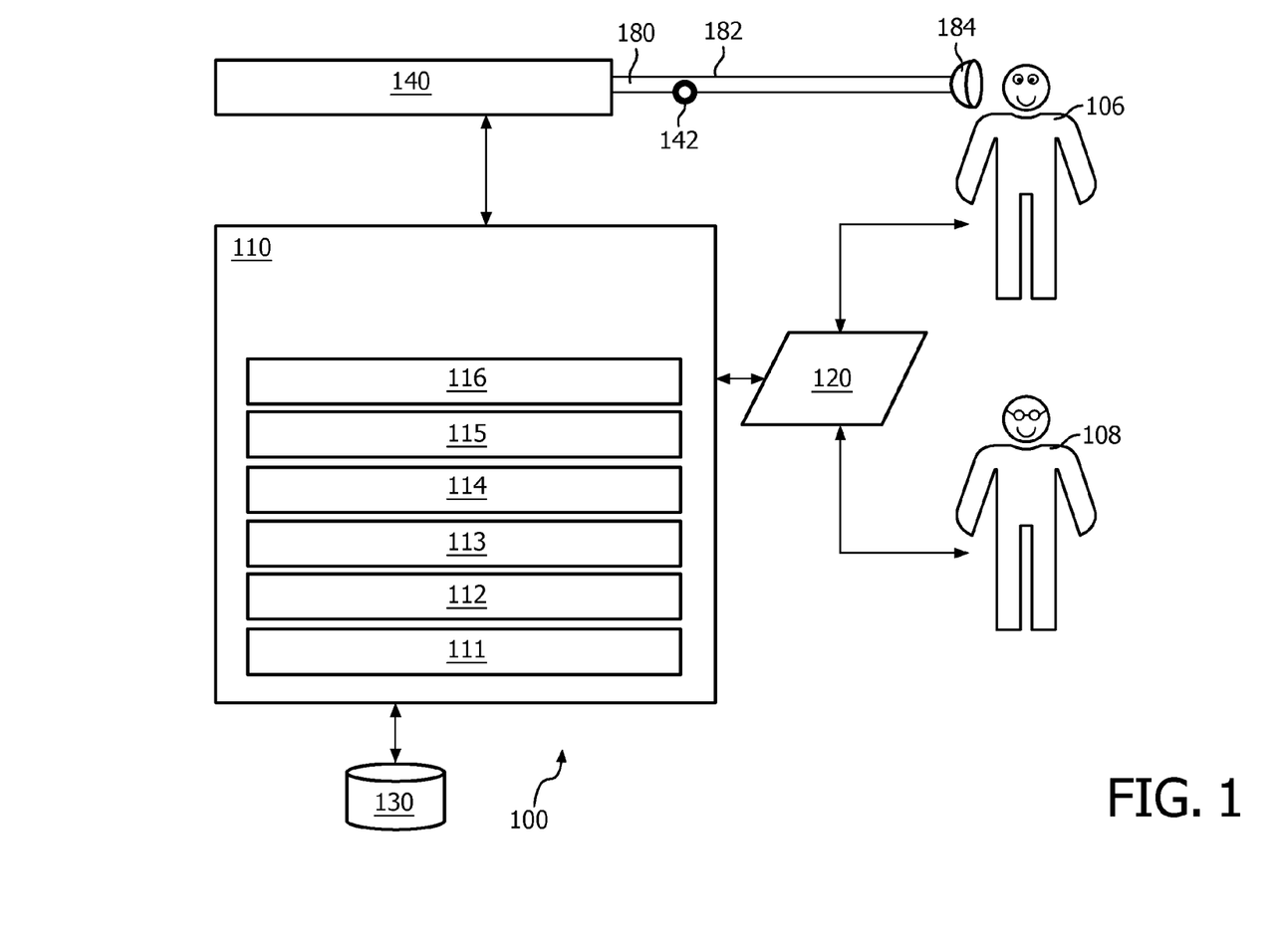
FIG. 1 schematically illustrates a system configured to measure respiratory parameters during application of non-invasive respiratory therapy of a subject, according to certain embodiments.

FIG. 1 schematically illustrates a system 100 configured to measure respiratory parameters during application of non-invasive respiratory therapy of a subject 106, according to certain embodiments. System 100 may be implemented as, integrated with, and/or operating in conjunction with a respiratory therapy device.

System 100 may include one or more of a pressure generator 140, a subject interface 180, one or more sensors 142, an electronic storage 130, a user interface 120, a processor 110, a timing module 111, a passive compliance module 112, a passive resistance module 113, an active compliance module 114, an active resistance module 115, a flow module 116, and/or other components.

Pressure generator 140 may be integrated, combined, or connected with a ventilator and/or (positive) airway pressure device (PAP/CPAP/BiPAP®/etc.) and configured to provide a pressurized flow of breathable gas for delivery to the airway of subject 106, e.g. via subject interface 180. Subject 106 may or may not initiate one or more phases of respiration. Pressure support may be implemented as a higher and lower positive pressure of a (multi-level) PAP device. For example, to support inspiration, the pressure of the pressurized flow of breathable gas may be adjusted to an inspiratory pressure. Alternatively, and/or simultaneously, to support expiration, the pressure of the pressurized flow of breathable gas may be adjusted to an expiratory pressure. Other schemes for providing respiratory support through the delivery of the pressurized flow of breathable gas are contemplated. Pressure generator 140 may be configured to adjust pressure levels, flow, humidity, velocity, acceleration, and/or other parameters of the pressurized flow of breathable gas in substantial synchronization with the breathing cycle of the subject. In certain embodiments, pressure generator 140 is part of an airway pressure device configured to provide types of therapy other than positive airway support therapy.

A pressurized flow of breathable gas may be delivered from pressure generator 140 to the airway of subject 106 by a subject interface 180. Subject interface 180 may include a conduit 182 and/or a subject interface appliance 184. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 may be configured to deliver the pressurized flow of breathable gas to or near the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

Electronic storage 130 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more respiratory parameters (as discussed elsewhere herein), information indicating whether the subject adequately complied with a therapy regimen, information indicating whether and/or when a respiratory event occurred, and/or other information. Electronic storage 130 may be a separate component within system 100, or electronic storage 130 may be provided integrally with one or more other components of system 100 (e.g., processor 110).

User interface 120 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to subject 106 is a report detailing the changes in determined lung mechanics throughout a period during which the subject is receiving therapy. An example of information that may be conveyed by subject 106 and/or user 108 is the breathing mode of subject 106, i.e. spontaneous or non-spontaneous. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to subject 106 by user interface 120 in the form of auditory signals, visual signals, tactile signals, and/or other sensory signals.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to subject 106 information related to breathing and/or the pressurized flow of breathable gas. Note that the subject and the user of system 100 may be one and the same person.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor(s) 142 may be configured to generate output signals conveying measurements related to parameters of respiratory airflow or airway mechanics. These parameters may include one or more of flow, (airway) pressure, humidity, velocity, acceleration, and/or other parameters. Sensor 142 may be in fluid communication with conduit 182 and/or subject interface appliance 184.

The illustration of sensor 142 including a single member in FIG. 1 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the delivery of the gas to the airway of subject 106, lung mechanics of subject 106, and/or a respiratory effort by the subject. For example, a parameter may be related to a mechanical unit of measurement of a component of pressure generator 140 (or of a device that pressure generator 140 is integrated, combined, or connected with) such as rotor speed, motor speed, blower speed, fan speed, or a related measurement that may serve as a proxy for any of the previously listed parameters through a previously known and/or calibrated mathematical relationship. Resulting signals or information from sensor 142 may be transmitted to processor 110, user interface 120, electronic storage 130, and/or other components of system 100. This transmission can be wired and/or wireless.

Processor 110 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of timing module 111, passive compliance module 112, passive resistance module 113, active compliance module 114, active resistance module 115, flow module 116, and/or other modules. Processor 110 may be configured to execute modules 111, 112, 113, 114, 115, and/or 116 by software; hardware; firmware; some combination of software, hardware, and/or firmware; and/or other mechanisms for configuring processing capabilities on processor 110.

It should be appreciated that although modules 111, 112, 113, 114, 115, and 116 are illustrated in FIG. 1 as being co-located within a single processing unit, in implementations in which processor 110 includes multiple processing units, one or more of modules 111, 112, 113, 114, 115, and/or 116 may be located remotely from the other modules. The description of the functionality provided by the different modules 111, 112, 113, 114, 115, and/or 116 described below is for illustrative purposes, and is not intended to be limiting, as any of modules 111, 112, 113, 114, 115, and/or 116 may provide more or less functionality than is described. For example, one or more of modules 111, 112, 113, 114, 115, and/or 116 may be eliminated, and some or all of its functionality may be provided by other ones of modules 111, 112, 113, 114, 115, and/or 116. Note that processor 110 may be configured to execute one or more additional modules that may perform some or all of the functionality attributed below to one of modules 111, 112, 113, 114, 115, and/or 116.

One or more modules may be configured to determine one or more gas parameters, breathing parameters, and/or other parameters from output signals generated by sensor(s) 142. One or more gas parameters may be related to and/or derived from measurements of one or more of (peak) flow, flow rate, (tidal) volume, pressure, temperature, humidity, velocity, acceleration, gas composition (e.g. concentration(s) of one or more constituents), thermal energy dissipated, (intentional) gas leak, and/or other measurements related to the (pressurized) flow of breathable gas. One or more breathing parameters may be derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters. Some or all of this functionality may be incorporated or integrated into other computer program modules of processor 110.

Timing module 111 is configured to determine respiratory timing parameters and/or other timing parameters related to the operation of system 100, such as transitions in breathing between inhalations and exhalations. Respiratory timing parameters may include transitional moments that separate inhalation phases from exhalation phases and vice versa, breathing period, respiratory rate, inhalation time or period, exhalation time or period, start and/or end of inhalation phases, start and/or end of exhalation phases, and/or other respiratory timing parameters. Timing parameters related to the operation of system 100 may include therapy session length, average and/or cumulative daily and/or nightly usage, amount of usage since the most recent pressure adjustment, and/or other timing parameters related to the operation of system 100.

Figure 3A:
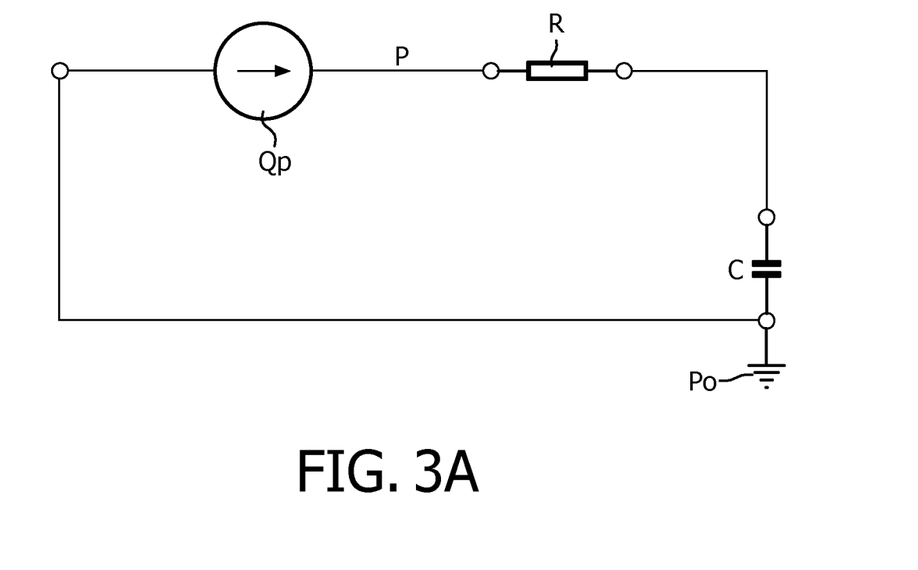
FIG. 3A-3B illustrate standard lung models.

Passive compliance module 112 is configured to determine a passive exhalation lung compliance during an exhalation. Passive compliance module 112 may be configured to determine a passive inhalation lung compliance during an inhalation. The inhalation and exhalation may be demarcated based on the transitions as determined by timing module 111. Determination may be dynamic, i.e. per breathing cycle and/or phase. Determination by the passive compliance module is based on a passive lung model. A passive lung model may comprise a serial (fluid) coupling of a flow source (e.g., a ventilator), a lung resistance, and a lung compliance. By way of illustration, FIG. 3A illustrates a standard passive lung model, including a flow source labeled $Q_P$, a proximal pressure labeled P, a lung resistance labeled R, a lung compliance labeled C, and an end expiratory pressure labeled $P_0$. Proximal pressure and subject flow may be related as follows:

$P = R \cdot Q_P/1000 + V/C + P_0$, wherein the unit of pressure may be cmH$_2$O, V may be subject volume in ml, which may be obtained independently, e.g., for each breath. By obtaining, estimating, and/or determining the proximal (or airway) pressure of the subject (e.g., at the start of an inhalation), the subject flow, and the pressure $P_0$ at the end of an exhalation directly following the inhalation, lung compliance and lung resistance may be determined, calculated and/or estimated, using the formula above. Note that leaks in the respiratory circuit are not explicitly accounted for in the formula above.

Flow module 116 is configured to determine the subject flow, while taking the presence of leaks into account. Subsequently, the passive lung model, as used by multiple modules in system 100, may be based on the subject flow determined by flow module 116. Determination of the subject flow may be based on circuit flow, which may in turn be determined based on output signals generated by sensors conveying measurements related to parameters of respiratory airflow or airway mechanics.

Leaks may include intentional or non-intentional leaks, known or unknown leaks, variable or non-variable leaks, and/or other leaks. For example, subject interface 184 may be a mask having an unintentional mask leak, intentional and/or controllable exhalation port leak, and/or other leaks. Other components of system 100 may include known and/or predictable leaks, such as the connections of pressure generator 140 to other components of system 100. The instantaneous estimated estimate subject flow $Q_P(t)$ and the instantaneous total circuit leak $Q_{Leak}(t)$ may be summed according to the following two formulae:

$Q_P(t) = Q_C(t) - Q_{Leak}(t)$ and $Q_{Leak}(t) = Q_{L_{known}}(t) + Q_{L_{unknown}}(t)$, wherein $Q_C(t)$ represents the circuit flow in the respiratory circuit, $Q_{L_{known}}(t)$ represents the instantaneous known circuit leak, which may include intentional leaks and a systemic leak flow that predictably varies with a given proximal pressure, and $Q_{L_{unknown}}(t)$ represents the instantaneous unknown circuit leak, which may include an unintentional leak at or near a leak orifice of the subject. The systemic leak flow may be characterized and pre-stored in, e.g., electronic storage 130. The unknown leak may be modeled as:

$$Q_{L_{unknown}}(t) = \frac{\sqrt{P(t)}}{\sqrt{R_{L_{unknown}}}},$$

wherein P(t) is the proximal pressure and $$\frac{1}{\sqrt{R_{L_{unknown}}}}$$

represents the average resistance of the leak orifice of the subject, which may be determined using the following formula, e.g., for each breath:

$$\frac{1}{\sqrt{R_{L_{unknown}}}} = \frac{\int_{t_0}^{t_2} [Q_C(t) - Q_{L_{unknown}}(P(t))] dt}{\int_{t_0}^{t_2} \sqrt{P(t)}\, dt}$$

wherein $t_0$ is the start of an inhalation and $t_2$ is the end of the subsequent exhalation. The average resistance of the leak orifice of the subject may change over time, e.g. between breaths. Accordingly, the resistance of the leak orifice could be determined regularly, e.g., for every breath, every ten seconds, every minute, and/or using any other regular and/or recurring determination. Through substitution, the instantaneous estimated estimate subject flow $Q_P(t)$ may be determined using the following formula:

$$Q_P(t) = Q_C(t) - Q_{L_{known}}(P(t)) - \frac{\int_{t_0}^{t_2} [Q_C(t) - Q_{L_{known}}(P(t))] dt}{\int_{t_0}^{t_2} \sqrt{P(t)}\, dt} \sqrt{P(t)}$$

Passive compliance module 112 is configured to use the passive lung model, in particular the estimated estimate subject flow $Q_P(t)$, to determine the passive exhalation lung compliance as follows: Suppose the estimated proximal pressure is given by $P_{est} = R \cdot Q_P/1000 + V/C + P_0$, and P represents the measured proximal pressure, $P_{diff}$ represents the difference between P and $P_0$. Using the least square method (and/or another suitable method to calculate C) minimizes the sum of the squared difference between measured and estimated pressure:

$$S = \sum (P_{est} - P)^2 = \sum \left( R^2(Q_P/1000)^2 + \frac{2R}{C}(Q_P/1000)V + \frac{V^2}{C^2} \right) - 2\sum \left( R(Q_P/1000)P_{diff} + \frac{VP_{diff}}{C} \right) + \sum P_{diff}^2$$

Solving for C results in the following:

$$C = \frac{m1 * m1 - m2 * m3}{m4 * m1 - m5 * m3}$$

where 
$$\begin{cases} m1 = \sum (Q_P/1000)V \\ m2 = \sum V^2 \\ m3 = \sum (Q_P/1000)^2 \\ m4 = \sum P_{diff}(Q_P/1000) \\ m5 = \sum P_{diff} V \end{cases}$$

Note that parameters m1 through m5 are set to zero at the start of the exhalation. The formula above can be used to determine the passive exhalation lung compliance. To determine the passive inhalation lung compliance, volume V and parameters m1 through m5 are set to zero at the start of the inhalation. The circuit flow $Q_C$ and proximal pressure P are obtained, e.g., through sensors in system 100, and the formula above can be used to determine the passive inhalation lung compliance. To determine both the passive exhalation lung compliance and the passive inhalation lung compliance, passive compliance module 112 may be configured to determine the passive inhalation lung compliance first, before determining the passive exhalation lung compliance, e.g. such that the exhalation used for determination immediately follows the inhalation used for determination.

Passive resistance module 113 is configured to determine a passive exhalation lung resistance during the exhalation, wherein the determination by the passive resistance module is based on a passive lung model. Passive resistance module 113 may be configured to determine a passive inhalation lung resistance. The resistance, for either breathing phase, may be the maximum pressure drop over the maximum flow rate that passes the airway of the subject. In other words: $R=\Delta P_{max}/Q_{P_{max}}$. Using the passive lung compliance as determined by passive compliance module 112, the subject lung pressure $P_{Lung}$ may be calculated using $P_{Lung}=V/C+P_0$, such that the pressure drop $\Delta P$ is $\Delta P=P-P_{Lung}=P_{diff}-V/C$. Assuming that the pressure drop increases or decreases monotonically with $Q_P$, $\Delta P_{max}$ occurs at the moment when subject flow reaches its maximum value. For that reason the passive resistance may be rewritten as follows:

$$R = \frac{(P_{diff} - V/C)|_{max}}{Q_P|_{when\ (P_{diff}-V/C)|_{max}}}$$

This formula applies to the passive exhalation lung resistance by using the passive exhalation lung compliance (e.g., from passive compliance module 112) and the maximum pressure drop $\Delta P_{max}$ during the exhalation. This formula applies to the passive inhalation lung resistance by using the passive inhalation lung compliance (e.g., from passive compliance module 112) and the maximum pressure drop $\Delta P_{max}$ during the inhalation. To determine both the passive exhalation lung resistance and the passive inhalation lung resistance, passive resistance module 113 may be configured to determine the passive inhalation lung resistance first, before determining the passive exhalation lung resistance, e.g. such that the exhalation used for determination immediately follows the inhalation used for determination.

Active compliance module 114 is configured to determine an active lung compliance that reflects an active lung model, wherein the active lung compliance is determined based on the passive exhalation lung compliance and a subject breathing mode. Determination of the active lung compliance may further be based on the passive inhalation lung compliance. The subject breathing mode may be a spontaneous breathing mode or a non-spontaneous breathing mode. System 100 may obtain the subject breathing mode, e.g. as a system setting and/or user input, and/or determine the subject breathing mode, e.g. through analysis of output signals generated by one or more sensors of system 100.

Figure 3B:
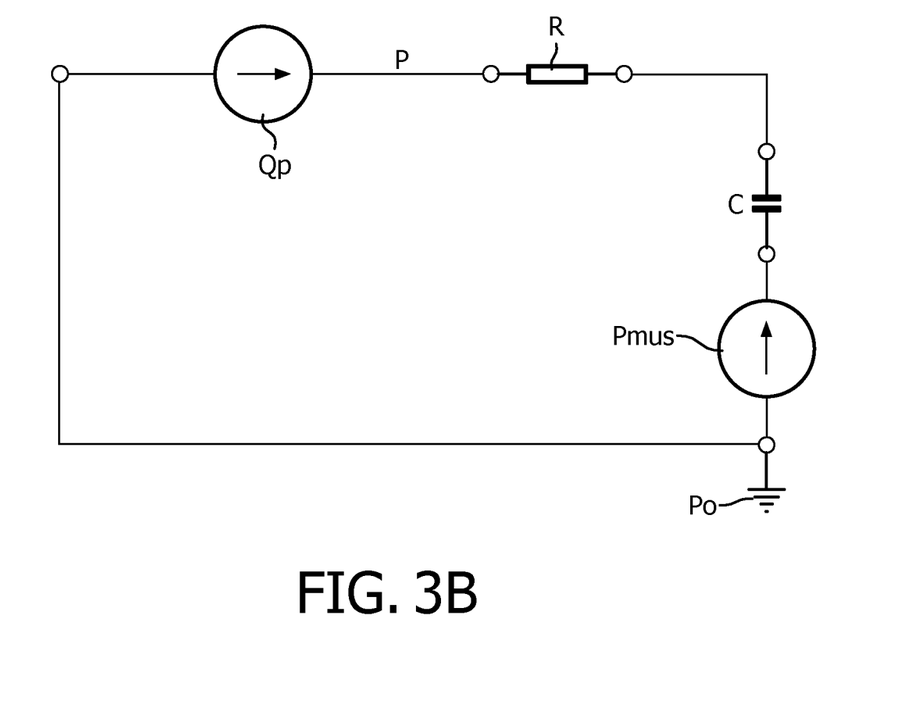

By way of illustration, FIG. 3B illustrates a standard active lung model, which differs from a standard passive lung model (e.g., see FIG. 3A) at least due to "interference" by spontaneous breathing of the subject and/or inspiratory muscle pressure of the subject, represented by $P_{mus}$. Notably, though, during exhalation, the interference of $P_{mus}$ may be substantially negligible, as the lung of the subject may be passively relaxed during exhalation. For this reason, (dynamic) determination of the active lung compliance and active lung resistance spanning an entire breathing cycle may be accomplished by (dynamically) determining compliance and resistance separately during inhalation and exhalation, and subsequently combining the results depending on the breathing mode of the subject.

Active compliance module 114 may determine the active compliance C of the subject by combining the passive exhalation lung compliance $C_{exh}$ and the passive inhalation lung compliance $C_{inh}$ according to: $C=\text{weight}*C_{inh}+(1-\text{weight})*C_{exh}$, wherein weight is, e.g., 0 for spontaneous breathing mode, and, e.g., 0.5 for non-spontaneous breathing mode. The value for weight should be between 0 and 1.

Active resistance module 115 is configured to determine an active lung resistance that reflects an active lung model (e.g., the standard active lung model of FIG. 3B), wherein the active lung resistance is determined based on the passive exhalation lung resistance and the subject breathing mode. Determination of the active lung resistance may further be based on the passive inhalation lung resistance. Active resistance module 115 may determine the active resistance R of the subject by combining the passive exhalation lung resistance $R_{exh}$ and the passive inhalation lung resistance $R_{inh}$ according to: $R=\text{weight}*R_{inh}+(1-\text{weight})*R_{exh}$, wherein weight is, e.g., 0 for spontaneous breathing mode, and, e.g., 0.5 for non-spontaneous breathing mode. The value for weight should be between 0 and 1.

Figure 2:
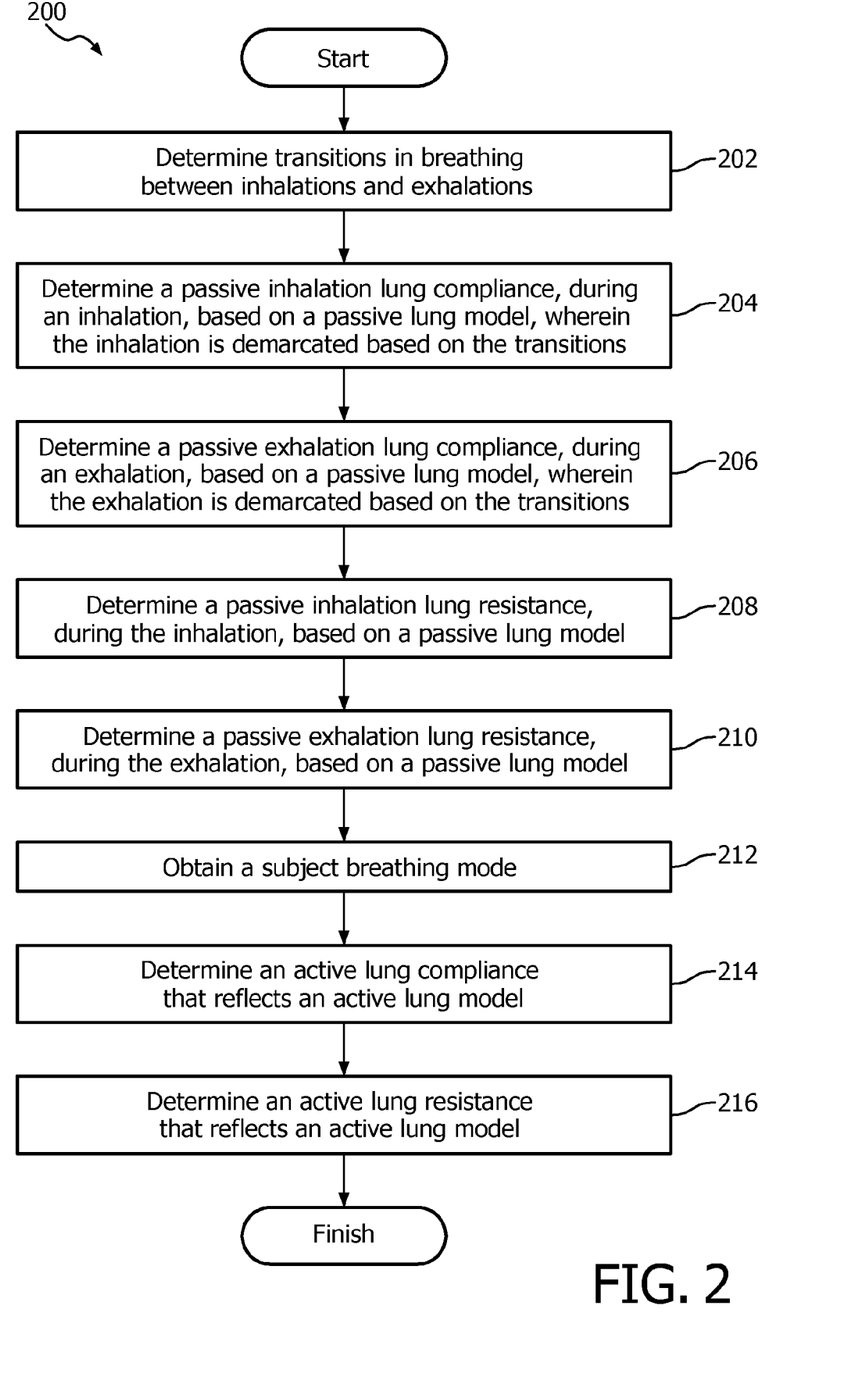
FIG. 2 illustrates a method for measuring respiratory parameters during non-invasive respiratory therapy of a subject, according to certain embodiments.

FIG. 2 illustrates a method 200 for measuring respiratory parameters during non-invasive respiratory therapy of a subject. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, transitions in breathing between inhalations and exhalations are determined. In one embodiment, operation 202 is performed by a timing module similar to or substantially the same as timing module 111 (shown in FIG. 1 and described above).

At an operation 204, a passive inhalation lung compliance is determined, during an inhalation, based on a passive lung model, wherein the inhalation is demarcated based on the transitions. In one embodiment, operation 204 is performed by a passive compliance module similar to or substantially the same as passive compliance module 112 (shown in FIG. 1 and described above).

At an operation 206, a passive exhalation lung compliance is determined, during an exhalation, based on a passive lung model, wherein the exhalation is demarcated based on the transitions. In one embodiment, operation 206 is performed by a passive compliance module similar to or substantially the same as passive compliance module 112 (shown in FIG. 1 and described above).

At an operation 208, a passive inhalation lung resistance is determined, during an inhalation, based on a passive lung model. In one embodiment, operation 208 is performed by a passive resistance module similar to or substantially the same as passive resistance module 113 (shown in FIG. 1 and described above).

At an operation 210, a passive exhalation lung resistance is determined, during an exhalation, based on a passive lung model. In one embodiment, operation 210 is performed by a passive resistance module similar to or substantially the same as passive resistance module 113 (shown in FIG. 1 and described above).

At an operation 212, a subject breathing mode is obtained. In one embodiment, operation 212 is performed through a user interface to or substantially the same as user interface 120 (shown in FIG. 1 and described above).

At an operation 214, an active lung compliance that reflects an active lung model is determined. In one embodiment, operation 214 is performed by an active compliance module similar to or substantially the same as active compliance module 114 (shown in FIG. 1 and described above).

At an operation 216, an active lung resistance that reflects an active lung model is determined. In one embodiment, operation 216 is performed by an active resistance module similar to or substantially the same as active resistance module 116 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to measure respiratory parameters during application of non-invasive respiratory therapy of a subject, the system comprising:
a non-invasive respirator configured to ventilate the subject, the non-invasive respirator comprising one or more processors configured to execute computer program modules, wherein the computer program modules comprise:
a timing module configured to determine transitions in breathing between inhalations and exhalations;
a passive compliance module configured to determine a passive exhalation lung compliance during an exhalation, wherein the determination by the passive compliance module is based on a passive lung model, and wherein the exhalation is demarcated based on the transitions;
a passive resistance module configured to determine a passive exhalation lung resistance during the exhalation, wherein the determination by the passive resistance module is based on the passive lung model;
an active compliance module configured to determine an active lung compliance that reflects an active lung model, wherein the active lung compliance is determined based on the passive exhalation lung compliance and a weight factor, the weight factor based on an obtained subject breathing mode;
an active resistance module configured to determine an active lung resistance that reflects the active lung model, wherein the active lung resistance is determined based on the passive exhalation lung resistance and a weight factor, the weight factor based on the obtained subject breathing mode;
a flow module configured to determine an instantaneous estimated subject flow, wherein the flow module takes a presence of both (i) instantaneous known respiratory circuit leaks and (ii) instantaneous unknown respiratory circuit leaks into account to determine the instantaneous estimated subject flow; and
a user interface configured to communicate to a user one or more of the determined respiratory parameters during a period of respiratory therapy.

2. The system of claim 1, wherein the passive compliance module is further configured to determine a passive inhalation lung compliance during an inhalation, wherein the inhalation is demarcated based on the transitions, wherein the passive resistance module is further configured to determine a passive inhalation lung resistance during the inhalation, wherein the determination by the active compliance module is further based on the passive inhalation lung compliance, and wherein the determination by the active resistance module is further based on the passive inhalation lung resistance.

3. The system of claim 1, wherein the flow module is further configured to determine a breath-by-breath subject flow based on a respiratory circuit flow, wherein the passive lung model is based on the determined breath-by-breath subject flow.

4. The system of claim 3, wherein application of the non-invasive respiratory therapy includes a systemic leak, wherein the systemic leak includes a known circuit leak and an unknown leak at or near a leak orifice of the subject, and wherein determination by the flow module of the breath-by-breath subject flow is further based on the systemic leak.

5. The system of claim 4, wherein the unknown leak at or near the leak orifice of the subject is based on an average resistance of the leak orifice.

6. The system of claim 5, wherein the average resistance of the leak orifice is determined based on the transitions in breathing between inhalations and exhalations.

7. The system of claim 1, wherein the subject breathing mode is a spontaneous breathing mode or a non-spontaneous breathing mode.

8. A method for measuring respiratory parameters during non invasive respiratory therapy of a subject, the method comprising:
providing a non-invasive respirator configured to ventilate the subject via a subject breathing mode, the non-invasive respirator comprising a processor;

determining, by the processor, transitions in breathing between inhalations and exhalations;

determining, by the processor, a passive exhalation lung compliance, during an exhalation, based on a passive lung model, wherein the exhalation is demarcated based on the transitions;

determining, by the processor, a passive exhalation lung resistance, during the exhalation, based on the passive lung model;

determining, by the processor, an active lung compliance that reflects an active lung model, wherein the determination is based on the passive exhalation lung compliance and a weight factor, the weight factor based on the subject breathing mode;

determining, by the processor, an active lung resistance that reflects the active lung model, wherein the determination is based on the passive exhalation lung resistance and the weight factor based on the subject breathing mode;

determining, by the processor, an instantaneous estimated subject flow, wherein determining the instantaneous estimated subject flow takes a presence of both (i) instantaneous known respiratory circuit leaks and (ii) instantaneous unknown respiratory circuit leaks into account to determine the instantaneous estimated subject flow; and communicating, to a user via a user interface, one or more of the determined respiratory parameters during a period of respiratory therapy.

9. The method of claim 8, further comprising:

determining a passive inhalation lung compliance, during an inhalation, wherein the inhalation is demarcated based on the transitions; and determining a passive inhalation lung resistance, during the inhalation, wherein determining the active lung compliance is further based on the passive inhalation lung compliance, and wherein determining the active lung resistance is further based on the passive inhalation lung resistance.

10. The method of claim 8, further comprising:

obtaining a respiratory circuit flow of the non-invasive respiratory therapy of the subject; and determining a breath-by-breath subject flow based on the respiratory circuit flow, wherein the passive lung model is based on the determined breath-by-breath subject flow.

11. The method of claim 10, wherein application of the non-invasive respiratory therapy includes a systemic leak, wherein the systemic leak includes a known circuit leak and an unknown leak at or near a leak orifice of the subject, and wherein determining the breath-by-breath subject flow is further based on the systemic leak.

12. The method of claim 11, further comprising:

determining the unknown leak at or near the leak orifice of the subject based on an average resistance of the leak orifice.

13. The method of claim 12, further comprising:

determining the average resistance of the leak orifice based on the transitions in breathing between inhalations and exhalations.

14. The method of claim 8, wherein the subject breathing mode is a spontaneous breathing mode or a non-spontaneous breathing mode.

15. A system configured for measuring respiratory parameters during application of non-invasive respiratory therapy of a subject, the system comprising a non-invasive respirator configured to ventilate the subject using a subject breathing mode, the non-invasive respirator comprising:

means for determining transitions in breathing between inhalations and exhalations;

means for determining a passive exhalation lung compliance, during an exhalation, based on a passive lung model, wherein the exhalation is demarcated based on the transitions;

means for determining a passive exhalation lung resistance, during the exhalation, based on the passive lung model;

means for determining an active lung compliance, reflecting an active lung model, based on the passive exhalation lung compliance and a weight factor, the weight factor based on the subject breathing mode;

means for determining an active lung resistance, reflecting the active lung model, based on the passive exhalation lung resistance and a weight factor, the weight factor based on the subject breathing mode;

means for determining an instantaneous estimated subject flow, wherein determining the instantaneous estimated subject flow takes a presence of both (i) instantaneous known respiratory circuit leaks and (ii) instantaneous unknown respiratory circuit leaks into account to determine the instantaneous estimated subject flow; and means for communicating, to a user via a user interface, one or more of the determined respiratory parameters during a period of respiratory therapy.

16. The system of claim 15, further comprising:

means for determining a passive inhalation lung compliance, during an inhalation, wherein the inhalation is demarcated based on the transitions; and means for determining a passive inhalation lung resistance, during the inhalation, wherein operation of the means for determining the active lung compliance is further based on the passive inhalation lung compliance, and wherein operation of the means for determining the active lung resistance is further based on the passive inhalation lung resistance.

17. The system of claim 15, further comprising:

means for obtaining a respiratory circuit flow of the non-invasive respiratory therapy of the subject; and means for determining a breath-by-breath subject flow based on the respiratory circuit flow, wherein the passive lung model is based on the determined breath-by-breath subject flow.

18. The system of claim 17, wherein application of the non-invasive respiratory therapy includes a systemic leak, wherein the systemic leak includes a known circuit leak and an unknown leak at or near a leak orifice of the subject, and wherein operation of the means for determining the breath-by-breath subject flow is further based on the systemic leak.

19. The system of claim 18, further comprising:

means for determining the unknown leak at or near the leak orifice of the subject based on an average resistance of the leak orifice.

20. The system of claim 19, further comprising:

means for determining the average resistance of the leak orifice based on the transitions in breathing between inhalations and exhalations.

* * * * *